Figure 1:
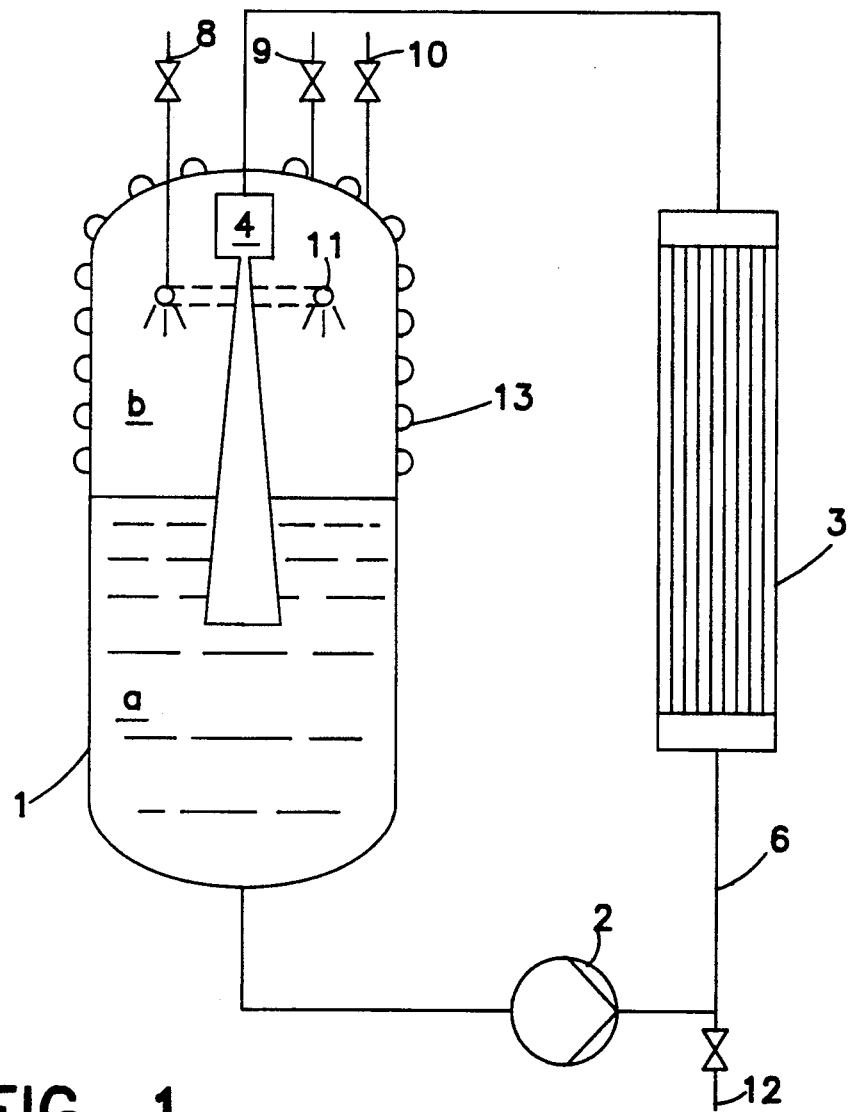

United States Patent [19]

Leuteritz

[11] Patent Number: 5,159,092

[45] Date of Patent: Oct. 27, 1992

[54] PROCESS FOR THE SAFE AND ENVIRONMENTALLY SOUND PRODUCTION OF HIGHLY PURE ALKYLENE OXIDE ADDUCTS

[75] Inventor: Günter M. Leuteritz, Pratteln, Switzerland

[73] Assignee: Buss AG, Pratteln, Switzerland

[21] Appl. No.: 581,112

[22] Filed: Sep. 12, 1990

[30] Foreign Application Priority Data

Sep. 22, 1989 [CH] Switzerland .................. 3586/89

[51] Int. Cl.⁵ ............................. C07C 51/00
[52] U.S. Cl. ........................ 554/149; 554/160; 554/167; 562/557
[58] Field of Search .................. 260/410; 564/505

[56] References Cited

U.S. PATENT DOCUMENTS 2,586,767  1/1948  Wilson ........................... 564/505

Primary Examiner—Jose G. Dees
Assistant Examiner—Deborah D. Carr
Attorney, Agent, or Firm—Wenderoth, Lind & Ponack

[57] ABSTRACT

An alkylene oxide is reacted in a loop reactor with an organic compound having a reactive hydrogen atom, a gas circulation and a liquid circulation around the reactor being provided and being coupled with one another via an ejector mixing nozzle. To ensure completeness of the reaction and suppression of the formation of by-products such as dioxane, it is essential to reduce the temperature of the entire alkylene oxide gas phase to a temperature below that of the liquid phase, and this is effected by feeding and evaporating liquid alkylene oxide and by cooling of the gas phase on the unit walls.

13 Claims, 2 Drawing Sheets

PROCESS FOR THE SAFE AND ENVIRONMENTALLY SOUND PRODUCTION OF HIGHLY PURE ALKYLENE OXIDE ADDUCTS

The invention relates to a process for the production of alkylene oxide adducts of organic compounds containing at least one reactive hydrogen atom which is linked via an oxygen, nitrogen or sulfur atom to an organic molecule radical.

The organic compounds used are liquid under the reaction conditions; by contrast, the alkylene oxides used are gaseous under the reaction conditions. The alkylene oxides which can be used are especially ethylene oxide, propylene oxide, butylene oxide and other alkylene oxides which boil below 200° C.

Alkylene oxides are highly reactive compounds which add to reactive organic compounds in a highly exothermic reaction. It is therefore important to ensure safe and sufficient removal of the heat of reaction. However, a particularly serious factor is that alkylene oxides can react explosively with air and can also themselves decompose explosively without action of air, for example above 450° C./10 bar.

For this reason, there have always been endeavors to react alkylene oxides with extreme exclusion of air, and in particular at the lowest possible controlled rates.

It is known to those skilled in the art, inter alia from the review by Winnacker/Küchler, Volume 7, Organische Technologie [Organic Technology] III, 4th edition, C. Hanser Verlag Munich Vienna 1986, pages 129 to 131, to effect the reaction between the starting compounds described above in a stirred kettle with or without inert gas blanketing, using alkaline or acidic catalysts at temperatures above 100° C. and below 200° C.

It is also known from U.S. Pat. No. 2,586,767, to effect the reaction in a loop reactor under otherwise identical conditions. In this process, the liquid starting component is sprayed by means of a circulation pump via a downstream heat exchanger through a spray nozzle in a finely distributed form into the gaseous alkylene oxide atmosphere of the reactor. The heat removal, which is markedly improved as compared with the stirred kettle, allows considerably shortened reaction times at conversion rates of the order of magnitude of, for example, 400 kg of ethylene oxide/m$^3$ of reactor volume and per hour.

As a modification of the process according to U.S. Pat. No. 2,586,767, a process is proposed in the paper "Evolution of Ethoxylation Plants for Nonionic Surfactants Production" (P. Straneo, C. Maffezoni and A. Marchegiano, Pressindustria Engineering and Plants S.p.A., Biassono, Italy, read at the World Surfactants Congress, May 6 to 10, 1984, at Munich), wherein the liquid starting component is likewise sprayed into the gaseous alkylene oxide atmosphere within a specific contactor. This process has the disadvantageous features of an uncooled gas phase, the formation of a further gas space not communicating with the contactor gas phase, and the omission of forced circulation of the liquid phase within the contactor as a consequence of the gravity-determined delivery of the liquid phase from the contactor to the reactor.

All the above processes have the common feature that the liquid starting product is introduced into one or more static, uncooled and insufficiently mixed gas phases of alkylene oxide with or without an inert gas fraction.

Furthermore, in the article "Der Buss-Schleifenreaktor in der Oel- und Fetthärtungsindustrie [The Buss Loop Reactor in the Oil- and Fat-hardening Industry]" (R. F. Duveen and G. Leuteritz, Buss AG Basel, in Fette, Seifen, Anstrichmittel 84, 511-515, 1st special issue 1982) a hydrogenation process is described in which an ejector mixing nozzle produces large phase exchange areas between reaction gas and liquid, the reaction gas fed in gaseous form inevitably being continuously mixed intensively with the inert gas, which may be present, and being circulated.

This process for reacting gases with liquids already has advantages in relation to the suggested application to alkoxylations, both with respect to product quality and space/time yield as well as operational safety, over the other abovementioned processes without gas and liquid circulations coupled to one another via an ejector mixing nozzle. Thus, at an achievable high space/time yield having values of up to 1500 kg of ethylene oxide and more per m$^3$ of reactor volume and per hour, a markedly improved product quality is obtained due to the very vigorous circulation of the liquid phase and also of the gas phase, with very exact temperature control.

In addition, it is described in Austrian Patent Specification 287,890 how, in another hydrogenation process for organic compounds, the suction pressure of the mixing nozzle can be adjusted by means of a restrictable and controlled hydrogen feed to the mixing nozzle, independently of the gas pressure above the liquid in the upper part of the autoclave, and both the reaction rate and the selectivity of certain reactions can be influenced in this way.

Furthermore, due to the constant intensive homogenization of the uniform gas phase in itself, like the liquid phase, as a consequence of the vigorous circulation, the safety of this process is very considerably improved since local inhomogeneities with respect to temperature, alkylene oxide concentration and catalyst concentration are avoided.

With respect to the freedom from toxic impurities in the end products, the demands of the market have recently become very drastically more stringent. In this connection, the reduction of the residual content of unconverted alkylene oxides and also of by-products forming from the alkylene oxides during the reaction by addition reactions and rearrangement reactions may be mentioned. In the manufacture of ethylene oxide adducts, these are in particular ethylene oxide itself, dioxane and dioxolane.

The action of an acidic medium, which may be, for example, an acidic catalyst or also an acidic reactant itself such as, for example, a fatty acid, promotes the formation of said by-products to an extreme extent.

In order to meet the regulations, now applying statutorily in many countries, on the protection of the consumer from substances injurious to health, the ethylene oxide content must be below 1 ppm and the dioxane content must be below 10 ppm.

Hitherto, it has usually been possible to achieve these low ethylene oxide and dioxane values only by expensive purification processes in separate units by means of additional process steps. With respect to the avoidance of the formation of dioxane, none of the processes of the state of the art can reach the currently demanded limits in the actual reaction step. In all cases, a time-consuming and expensive additional after-treatment, predominantly in separate equipment, is necessary for stripping out the toxic traces by means of a carrier gas treatment with, for example, steam and/or nitrogen in vacuo at high temperatures.

A further disadvantage is that the considerable quantities of waste gas arising in the carrier gas treatment must now be expensively purified, like the toxic waste gas quantities arising during production, in waste gas purification units operating by the scrubber principle or adsorption principle or by incineration.

The processes employed for the removal of the toxic impurities by means of carrier gas treatment or adsorption on molecular sieves, as proposed in German Offenlegungsschrift 3,740,695, can also contribute simultaneously, if necessary under changed conditions, to a marked improvement in the use properties of alkylene oxide adducts with respect to odor and color. The extreme importance of the improvement demanded in the use properties of the products themselves and also the stability of the products with regard to further reactions is also clearly evident from German Offenlegungsschrift 3,604,035, in which the addition of certain additives is suggested as a solution.

The invention is thus based on the object of producing highly pure products in accordance with the current purity requirements, and those to be expected in the future, by means of a safe and environmentally sound production process in a single stage in one plant and hence particularly economically.

Surprisingly, this can be achieved when the reaction is carried out in the already mentioned loop reactor with an integrated ejector mixing nozzle via coupled gas and liquid circulations, the gas phase of reaction gas alone or with an admixture of inert gas being maintained within the closed gas circulation during the addition reaction at temperatures below the temperature of the liquid phase. The temperature difference between the two phases should be at least about 1° C. The reaction gas is the particular alkylene oxide, whereas any desired gas which does not react with itself or the reactants under the reaction conditions can be used as the inert gas. Preferably, nitrogen or carbon dioxide is used as the inert gas.

On the basis of numerous investigations of the action of the catalysts, in particular of the acidic type, a person skilled in the art had hitherto to assume that the formation of by-products of the alkylene oxides, in particular of dioxane, takes place essentially in the liquid phase which is activated by the temperature and catalyst, as can be seen especially from German Offenlegungsschrift 2,300,248.

The temperature of the gas phase is reduced advantageously by the addition of liquid ethylene oxide into the gas space of the reactor. This addition can be carried out in any desired manner, advantageously by fine distribution, for example via a nozzle ring.

Additionally, the cooling of the gas phase can be intensified by utilizing the equipment walls as a cooling surface. Advantageously, this is effected by cooling of the reactor walls, if the ejector mixing nozzle is arranged inside (see FIG. 1).

Figure 2:
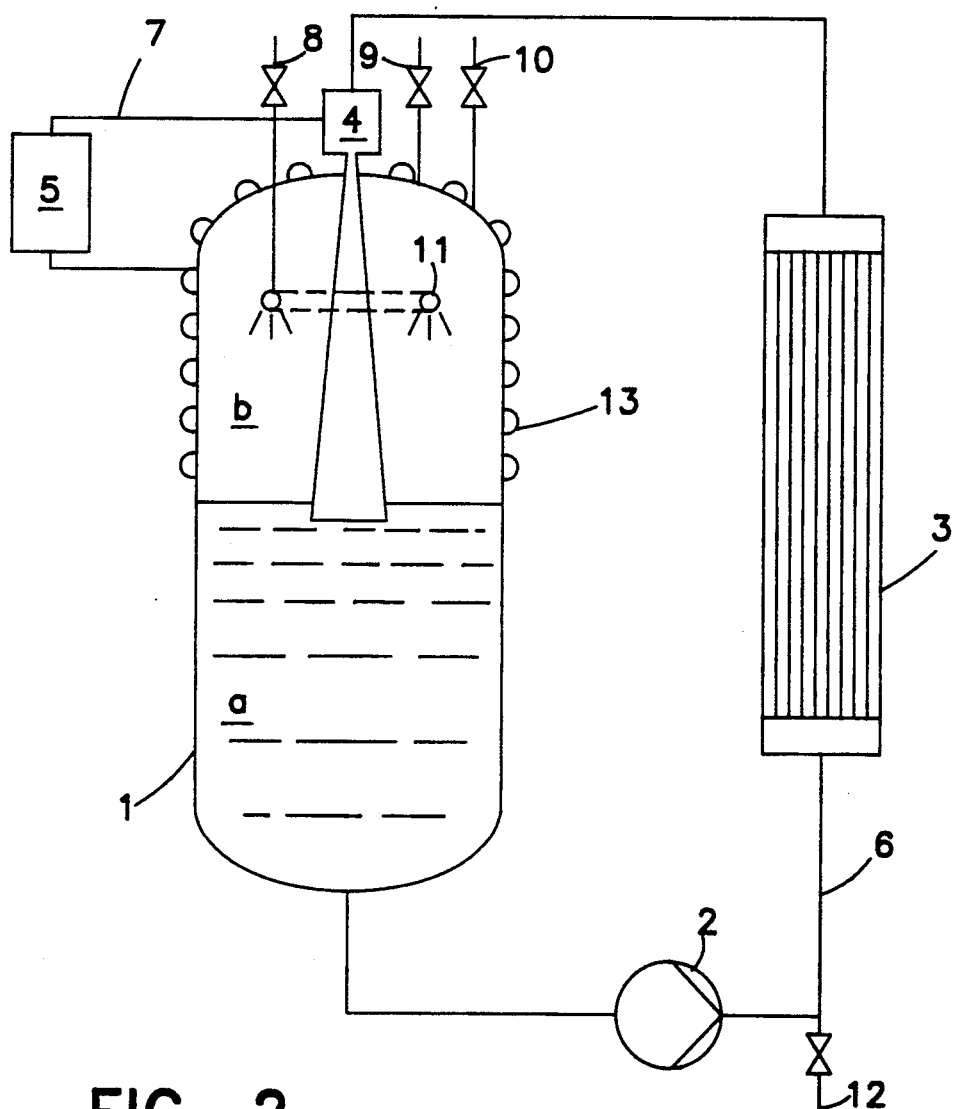

If the ejector mixing nozzle is arranged outside, both the connecting line between the reactor space and the ejector mixing nozzle and the heat exchanger, which may be installed, can be utilized additionally as cooling surfaces (see FIG. 2).

The process is advantageously carried out in equipment according to the attached FIG. 1 or FIG. 2. The numerals therein are defined as follows:

1: Reactor
2: Circulation pump
3: Liquid-phase heat exchanger
4: Ejector mixing nozzle
5: Gas-phase heat exchanger
6: Liquid-phase circulation line
7: Gas-phase circulation line
8: Liquid alkylene oxide feed line
9: Gas-phase discharge line
10: Inert gas feed line
11: Nozzle ring for liquid alkylene oxide
12: Liquid-phase feed and discharge line
13: Cooled reactor wall
a) Liquid phase
b) Gas phase It has proved to be particularly advantageous for the product quality if cooling of the gas phase is combined with vigorous mixing of the gas and liquid phases. For this purpose, it is necessary for the driving jet of the ejector to have an exit velocity of at least 10 m/second, preferably of more than 20 m/second, and for the circulation rate of the liquid phase to be such that the reactor contents are circulated at least 20 times per hour, preferably more than 30 times per hour, at all times during the reaction.

In addition, it has proved to be advantageous to set the inert gas partial pressure, from the start of the reaction, at least to a value above 80% of the alkylene oxide partial pressure, preferably to an inert gas partial pressure of from 1 to 25 bar, and especially to a pressure in the range from 3 to 7 bar.

As a result of these measures, individually or, if desired, also in parallel, it is possible, contrary to expectations, virtually completely to suppress the formation of toxic by-products of the alkylene oxides themselves and other by-products which adversely affect the use properties.

As compared with the processes of the state of the art, in which ethylene oxide values markedly above, 100 ppm and dioxane values in the range from 500 ppm to 2000 ppm are usually established in the ethoxylation in stirred kettle units, and ethylene oxide values above 10 ppm and dioxane values between 100 ppm and 1000 ppm are frequently unavoidable in loop reactors, depending on the process conditions and the type of product, ethylene oxide contents below 1 ppm and dioxane contents below 10 ppm are achieved by the process according to the invention.

Furthermore, the low temperature/time loading of the alkylene oxide gas phase leads to adducts which are particularly free of by-products, are light-colored and have a neutral odor.

Further advantages of the process according to the invention are the avoidance of large quantities of dioxane-containing waste gas, and a simultaneous increase in yield.

Furthermore, the process according to the invention represents a considerable gain in process engineering safety, since the alkylene oxide gas phase, which is at risk from autocatalytic decomposition, is at the same time also cooled by the gas circulation in addition to the forced homogenization, and the possibility of a hazardous decomposition is thus excluded.

The process according to the invention will be explained in more detail by reference to the examples which follow, complete conversion of the ethylene oxide and avoidance of the formation of dioxane being taken as characteristic of the effectiveness of the process.

COMPARISON EXAMPLE 1

Preparation of polyoxyethylene-20 lauryl ether in a stirred autoclave

In a stirred autoclave of 50 l useful capacity, which is provided with an inlet tube and a heating and cooling device, 9.3 kg of fatty alcohol (Lorol 1216, manufacturer: Henkel KGaA, Düsseldorf, Federal Republic of Germany; composition: about 62% of lauryl alcohol, 23% of myristyl alcohol) are charged and heated to 100° C. 0.04 kg of sodium hydroxide powder (98%) is then added as the catalyst and intensively mixed in. The autoclave is closed and the mixture is dried in vacuo. The vacuum is then broken with nitrogen, and the evacuation is repeated twice more, the vacuum being broken with nitrogen each time. Subsequently, the mixture is heated to 165° C. with stirring.

When this temperature has been reached, 0.15 kg of liquid ethylene oxide is added through the inlet tube which dips into the liquid, a maximum pressure of 4 bar being maintained in the autoclave. After 16 minutes, the start of the reaction is noticeable from a slight rise in temperature to 175° C. and a simultaneous drop pressure.

At this time, the addition of 42 kg of liquid ethylene oxide at a continuous feed rate of about 14 kg/hour is started, with continuous stirring and simultaneous cooling while observing the maximum reactor pressure. At the start of the addition phase, the pressure in the autoclave stabilizes at 3 bar and, at the end of the ethylene oxide addition, reaches a value of 4 bar. After completion of the ethylene oxide addition after about 3.5 hours, the reaction is allowed to continue for half an hour with stirring at the reaction temperature. The reactor pressure drops to 2.5 bar.

A sample is taken and examined by gas chromatography. This reaction product, a lauryl alcohol with 20 mol of added ethylene oxide, contained 130 ppm of ethylene oxide and 600 ppm of dioxane.

COMPARISON EXAMPLE 2

Preparation of polyoxyethylene-20 lauryl ether in the loop reactor according to U.S. Pat. No. 2,586,767

In a loop reactor according to U.S. Pat. No. 2,586,767, consisting of a reaction autoclave of 50 l useful capacity, a circulation pump, a heat exchanger and a spray device, the same products are charged in the same quantities as in Comparison Example 1 in the manner indicated therein, heated and dried. The reactor is closed, evacuated three times and the vacuum broken each time with nitrogen. The temperature is increased to 165° C. with circulation.

When this temperature is reached, the addition reaction is started with the addition of 300 g of liquid ethylene oxide within a period of 10 minutes, observing a maximum autoclave pressure of 4 bar. The start of the reaction is noticeable after 10 minutes from a rise in temperature by about 10° C. and a simultaneous decrease in the autoclave pressure at the end of this addition period.

After the start of the reaction, a further 42 kg of ethylene oxide are fed to the addition reaction at a feed rate of 17 kg/hour with continuous removal of the heat of reaction by cooling. The pressure in the unit rises from 3 bar in the first phase of the reaction to 4 bar at the end of the ethylene oxide addition. Within 10 minutes after the end of the ethylene oxide addition, the pressure in the unit falls to 2 bar.

At this time, a sample of the reaction product was taken and examined by gas chromatography. A content of 12 ppm of ethylene oxide and 46 ppm of dioxane was found.

COMPARISON EXAMPLE 3

Preparation of polyoxyethylene-20 lauryl ether in the loop reactor according to U.S. Pat. No. 2,586,767, supplemented by an ejector mixing nozzle arranged inside.

The unit according to Comparison Example 2 was modified by replacing the spray nozzle with an ejector mixing nozzle. Under otherwise identical conditions and using the same feed rates, the experiment according to Comparison Example 2 was carried out with the use of gaseous ethylene oxide in place of liquid ethylene oxide.

The pressure in the unit rose from an initial value of 2 bar at the start of the reaction to a value of 3.5 bar at the end of the ethylene oxide addition. After the end of the ethylene oxide addition, the pressure dropped back to 2 bar within 2 minutes.

After a further 8 minutes' circulation at 165° C., a sample was taken and analyzed. The ethylene oxide content was below 1 ppm, whereas the dioxane content was 18 ppm.

COMPARISON EXAMPLE 4

Preparation of polyoxyethylene-20 stearates in a stirred autoclave

In a stirred autoclave of 50 l useful capacity, which is provided with inlet tube and heating and cooling device, 12 kg of stearic acid (Edenor Stl, manufacturer: Henkel KGaA, Düsseldorf, Federal Republic of Germany; composition: about 46% of palmitic acid, 49% of stearic acid) are charged and heated to 100° C. 0.05 kg of sodium hydroxide powder (98%) is then added as the catalyst and intensively mixed in. The autoclave is closed and the mixture is dried in vacuo. The vacuum is then broken with nitrogen, and the evacuation is repeated twice more, the vacuum being broken with nitrogen each time. Subsequently, the mixture is heated to 165° C. with stirring.

When this temperature has been reached, the total quantity of 38 kg of ethylene oxide is added in portions as quickly as possible through the inlet tube, which dips into the liquid, while maintaining a maximum pressure of 6 bar in the autoclave.

The addition of the first 8 kg of ethylene oxide takes about 3 hours, while the remaining 30 kg of ethylene oxide are added in a further 4.5 hours. After the end of the ethylene oxide addition after about 7.5 hours, the reaction is allowed to continue with stirring for half an hour at the reaction temperature. The pressure in the reactor falls to about 3 bar.

A sample is taken and examined by gas chromatography. This reaction product, which is a stearic acid with 20 mol of adducted ethylene oxide, contained 150 ppm of ethylene oxide and about 3000 ppm of dioxane.

COMPARISON EXAMPLE 5

Preparation of a polyoxyethylene-20 stearate in the loop reactor according to U.S. Pat. No. 2,586,767

In a loop reactor according to Comparison Example 2, 12 kg of stearic acid (Edenor Stl manufactured by Henkel KGaA, Düsseldorf, Federal Republic of Germany; composition: 46% of palmitic acid and 49% of stearic acid) are charged together with 0.05 kg of NaOH powder (98%) as the catalyst at a temperature of 100° C., mixed and intensively dried. The reactor is closed and evacuated three times, and the vacuum being broken again with nitrogen each time. Subsequently, the temperature is raised to 165° C. while circulating and the reactor is at the same time evacuated once more.

When this temperature has been reached, the reaction is started by the addition of liquid ethylene oxide up to a pressure rise to 5.8 bar. The addition of 8 kg of ethylene oxide takes about 1.5 hours. At the end of this phase, a reactor pressure of 4.5 bar is established, and the remaining 30 kg of ethylene oxide are then added in the course of the next 3 hours. The reactor pressure was about 4.5 bar. The temperature of the product rose to 175° C.

0.5 hour after the end of the ethylene oxide feed, a sample was taken and analyzed. A residual ethylene oxide content of 95 ppm and a dioxane content of about 1400 ppm were determined.

EXAMPLE 1

Preparation of polyoxyethylene-20 lauryl ether in the loop reactor with an ejector mixing nozzle arranged outside and a nozzle ring arranged inside (FIG. 2).

The unit according to Comparison Example 3 was modified by moving the ejector mixing nozzle to the outside and fitting a pipe connection with heat exchanger between the gas space of the reactor and the suction branch of the ejector mixing nozzle. In addition, a nozzle ring for feeding liquid ethylene oxide was installed in the top space of the autoclave, in place of the simple inlet branch.

Under otherwise identical conditions and using the same quantities of materials, the experiment according to Comparison Example 3 was repeated. As the only modification of the experiment, the ethylene oxide was added not in gaseous form, but as a liquid; exit velocity of the driving jet 20 m/second and 30 circulations of the liquid (end volume) per hour. The reaction sequence was identical to that of Comparison Example 3.

The product sample, taken 10 minutes after the end of the ethylene oxide addition, contained less than 1 ppm of residual ethylene oxide, while the dioxane content was 5 ppm.

EXAMPLE 2

Preparation of a polyoxyethylene-20 stearate in the loop reactor (FIG. 1).

In a loop reactor according to FIG. 1, 12 kg of stearic acid (Edenox ST1 manufactured by Henkel KGaA, Düsseldorf, Federal Republic of Germany; composition: 46% of palmitic acid and 49% of stearic acid) are charged together with 0.05 kg of NaOH powder (98%) as the catalyst at a temperature of 100° C., mixed and intensively dried. The reactor is closed, and evacuated three times, the vacuum being broken again with nitrogen each time. The temperature is raised to 165° C., while circulating.

When this temperature is reached, the reaction is started by the addition of 1 kg of liquid ethylene oxide, with a pressure rise to 4.8 bar. A further 7 kg of ethylene oxide are added in the following 20 minutes. In this phase, a reactor pressure of 4.5 bar is established. The remaining 30 kg of ethylene oxide are then added in the course of the next 30 minutes. The reactor pressure moved between 4.5 and 4.0 bar. The temperature of the product rose to 175° C. After the end of the ethylene oxide addition, the pressure fell to 1.8 bar within one minute.

10 minutes after the end of the ethylene oxide feed, a sample was taken and analyzed. A residual ethylene oxide content of less than 1 ppm and a dioxane content of about 70 ppm were determined.

EXAMPLE 3

Preparation of a polyoxyethylene-25 nonylphenol ether in the loop reactor (FIG. 1)

In a loop reactor according to FIG. 1, 8.2 kg of nonylphenol together with 0.1 kg of Na methylate as the catalyst are charged at a temperature of 100° C., mixed and intensively dried. The reactor is closed and evacuated three times, the vacuum being broken again with nitrogen each time. The temperature is raised to 165° C., while circulating.

When this temperature is reached, 42 kg of liquid ethylene oxide are added immediately at a constant addition rate of 60 kg/hour. A pressure of 3.4 bar is established at the start, but this rises to 4.5 bar in the course of the reaction. At the same time, the product temperature rises to 175° C. After the end of the ethylene oxide addition, the pressure falls to 1.5 bar within one minute.

10 minutes after the end of the ethylene oxide addition, a sample was taken and analyzed. The residual ethylene oxide content was below 1 ppm and that of dioxane was 7 ppm.

EXAMPLE 4

Preparation of polyoxyethylene-20 lauryl ether in the loop reactor with an ejector mixing nozzle arranged outside and a nozzle ring arranged inside (FIG. 2).

In a unit according to Example 1 and under otherwise identical conditions and using the same quantities of materials as in Example 1, the experimental conditions were modified in such a way that, after flushing the unit twice with nitrogen before the start of the reaction, a nitrogen pressure of 3.5 bar in the unit was set when the vacuum was broken for the third time.

The pressure in the unit rose from an initial value of about 4.9 bar at the start of the reaction to a value of about 10.6 bar at the end of the ethylene oxide addition. After the end of the ethylene oxide addition, the pressure fell back to about 9.2 bar within 2 minutes.

The product sample taken 10 minutes after the end of the ethylene oxide addition had a residual ethylene oxide content below 1 ppm, while the dioxane content was below 3 ppm.

EXAMPLE 5

Preparation of polyoxyethylene-3 lauryl ether (FIG. 2)

28 kg of lauryl alcohol according to Comparison Example 1 and 0.15 kg of sodium methylate were weighed into a unit according to Example 1, heated to 100° C. while circulating and intensively mixed at the same time. The reaction mixture is dried by evacuation with circulation and maintaining the temperature. The vacuum is then broken with nitrogen and the evacuation is repeated twice more, the vacuum being broken again with nitrogen each time. Before the start of the ethylene oxide addition, the nitrogen pressure is raised to 2 bar and the temperature in the reactor is lowered to 80° C.

After the temperature of 80° C. has been reached, the addition of ethylene oxide is started immediately at an addition rate of 10 kg/h, while maintaining the temperature between 80 and 90° C. No induction period can be observed. Without interruption, the addition of ethylene oxide is continued up to a total quantity of 19.5 kg. After the end of the ethylene oxide addition, the temperature is briefly raised to 130° C. for 5 minutes and then lowered again to 80° C.

The pressure in the reactor was 3 bar at the start of the ethylene oxide addition and rose, as a result of the further addition, to 3.6 bar in the end phase of the ethylene oxide addition. After cooling to 80° C., the pressure in the reactor was again 2 bar.

Neither ethylene oxide with a detection sensitivity of 0.2 ppm nor dioxane with a detection sensitivity of 1 ppm were detectable in the reaction product, namely polyoxyethylene-3 lauryl ether.

What is claimed is:

1. A process for the safe and environmentally sound production of highly pure alkylene oxide adducts, having a residual ethylene oxide content of below 1 ppm and a residual dioxane content below 10 ppm without any after-treatment, which comprises reacting an alkylene oxide with an organic compound having at least one-reactive hydrogen atom in a loop reactor with gas and liquid circulations coupled via an ejector mixing nozzle, wherein firstly, the temperature of the entire gas phase in the head space of the reactor, consisting of alkylene oxide, or alkylene oxide and inert gas, is maintained at a temperature at least 1° C. lower, throughout the entire course of the reaction, than the liquid phase temperature anywhere in the reactor any time of the reaction, and secondly, enforcing a vigorous gas-phase turbulence and intermixing of gas and liquid phases by employing the ejector mixing nozzle driven by the circulating reaction liquid itself.

2. The process as claimed in claim 1, wherein the temperature of the gas phase is maintained below that of the liquid phase by removing thermal energy by means of evaporation of the liquid alkylene oxide.

3. The process as claimed in claim 2, wherein the evaporation of the alkylene oxide in the gas space of the reactor is effected by fine distribution of the liquid alkylene oxide.

4. The process as claimed in claim 2, wherein the temperature of the gas phase is maintained below that of the liquid phase additionally by removing thermal energy via plant walls which are in contact with and enclose the gas phase.

5. The process as claimed in claim 4, wherein the gas circulation is maintained by a connection routed outside the reactor between the gas space of the reactor and a suction branch of the ejector mixing nozzle, and said outside connection itself is designed as a heat exchanger.

6. The process as claimed in claim 1, wherein an ejector whose driving jet has an exit velocity of at least 10 m/second is used as a self-aspirating mixing nozzle.

7. The process as claimed in claim 6, wherein an ejector whose driving jet has an exit velocity of at least 20 m/second is used as the self-aspirating mixing nozzle.

8. The process as claimed in claim 1, wherein the liquid phase is circulated at such a rate that the reactor contents are circulated at least 10 times per hour at all times during the reaction.

9. The process as claimed in claim 8, wherein the liquid phase is circulated at such a rate that the reactor contents are circulated at least 30 times per hour at all times during the reaction.

10. The process as claimed in claim 1, wherein the inert gas partial pressure in the reactor is maintained during the reaction at at least 80% of the alkylene oxide partial pressure.

11. The process as claimed in claim 1, wherein the inert gas partial pressure in the reactor is 1 to 25 bar during the reaction.

12. The process as claimed in claim 11, wherein the inert gas partial pressure in the reactor is maintained in the range from 3 to 7 bar during the reaction.

13. The process as claimed in claim 3, wherein the fine distribution of the liquid alkylene oxide is effected by means of a nozzle ring.

* * * * *